(12) United States Patent
Olovsson et al.

(10) Patent No.: US 10,981,947 B2
(45) Date of Patent: Apr. 20, 2021

(54) AUTOMATIC GAS VALVE CONTAINER HOLDER FOR CHEMICAL SYNTHESIS

(71) Applicant: Cytiva Sweden AB, Uppsala (SE)

(72) Inventors: Bjorn Markus Olovsson, Uppsala (SE); Mathias Osmark, Stockholm (SE); Mangus Gamberg, Stockholm (SE); Daniel Carlsson, Stockholm (SE)

(73) Assignee: Cytiva Sweden AB, Uppsala (SE)

( * ) Notice: Subject to any disclaimer, the term of this patent is extended or adjusted under 35 U.S.C. 154(b) by 120 days.

(21) Appl. No.: 15/122,609

(22) PCT Filed: Mar. 12, 2015

(86) PCT No.: PCT/EP2015/055244
§ 371 (c)(1),
(2) Date: Aug. 30, 2016

(87) PCT Pub. No.: WO2015/136060
PCT Pub. Date: Sep. 17, 2015

(65) Prior Publication Data
US 2017/0066798 A1 Mar. 9, 2017

Related U.S. Application Data

(60) Provisional application No. 61/951,702, filed on Mar. 12, 2014.

(51) Int. Cl.
*C07K 1/04* (2006.01)
*B65B 31/04* (2006.01)
(Continued)

(52) U.S. Cl.
CPC .......... *C07K 1/045* (2013.01); *B01J 19/0046* (2013.01); *B65B 31/04* (2013.01); *C07K 1/063* (2013.01);
(Continued)

(58) Field of Classification Search
CPC . C07K 1/045; C07K 1/063; C07K 1/08; B01J 19/0046; B65B 31/04
(Continued)

(56) References Cited

U.S. PATENT DOCUMENTS 5,336,467 A * 8/1994 Heidt ............... G01N 35/00029
222/390
5,848,622 A * 12/1998 Kilcoin ................. B65B 31/047
141/59
(Continued)

FOREIGN PATENT DOCUMENTS

CN 103191580 A 7/2013
CN 103316726 A 9/2013
(Continued)

OTHER PUBLICATIONS

Japan Notice of Preliminary Rejection for Japanese Patent Application No. 2016556796, dated Feb. 12, 2019, 6 pages.
(Continued)

*Primary Examiner* — Benjamin R Whatley
*Assistant Examiner* — Jacqueline Brazin
(74) *Attorney, Agent, or Firm* — Eversheds Sutherland (US) LLP

(57) ABSTRACT

The invention relates to a container holder 10, comprising a main body 12 which in turn comprises a gas inlet 16; a solution liquid outlet 18; a gas control valve 20 through which a gas enters the container 100 from the gas inlet; and a sealing means 22 for the container, which sealing means includes a passageway 24 for the input of gas and output of a solution in the container via an egress tube 19; wherein when the container is connected to the container holder through the sealing means, the gas control valve opens automatically, and when the container is disconnected the gas control valve is closed automatically. The invention (Continued)

further relates to a container panel 50 which includes two or more container holders. Also disclosed are methods of using these containers and container panels for synthesizing a polypeptide.

20 Claims, 6 Drawing Sheets

(51) Int. Cl.
*B01J 19/00* (2006.01)
*C07K 1/06* (2006.01)
*C07K 1/08* (2006.01)

(52) U.S. Cl.
CPC ....... *C07K 1/08* (2013.01); *B01J 2219/00283* (2013.01); *B01J 2219/00308* (2013.01); *B01J 2219/00337* (2013.01); *B01J 2219/00346* (2013.01); *B01J 2219/00373* (2013.01); *B01J 2219/00389* (2013.01); *B01J 2219/00418* (2013.01); *B01J 2219/00585* (2013.01); *B01J 2219/00725* (2013.01)

(58) Field of Classification Search
USPC ........................................................ 422/561
See application file for complete search history.

(56) References Cited

U.S. PATENT DOCUMENTS

| | | | |
|---|---|---|---|
| 7,393,920 B2 | 7/2008 | Collins et al. | |
| 7,910,074 B2* | 3/2011 | Li | B01L 3/0203 222/61 |
| 2002/0090590 A1* | 7/2002 | Mosslang | A61C 1/0084 433/80 |
| 2006/0264779 A1* | 11/2006 | Kemp | A61B 5/1411 600/583 |
| 2011/0038351 A1 | 2/2011 | Sahara | |
| 2014/0273191 A1* | 9/2014 | Tipgunlakant | C12Q 1/02 435/288.4 |

FOREIGN PATENT DOCUMENTS

| | | |
|---|---|---|
| EP | 1992407 A1 | 11/2008 |
| JP | 2005-015483 A | 1/2005 |

OTHER PUBLICATIONS

International Search Report and Written Opinion regarding International Application No. PCT/EP2015/055244, dated Jun. 9, 2015, 9 pages.
First Office Action for Chinese Patent Appl. No. 201580013042.1, filed Mar. 12, 2015, 18 pages, dated Feb. 14, 2018.

* cited by examiner

AUTOMATIC GAS VALVE CONTAINER HOLDER FOR CHEMICAL SYNTHESIS

CROSS-REFERENCE TO RELATED APPLICATIONS

This application is a filing under 35 U.S.C. 371 of international application number PCT/EP2015/055244, filed Mar. 12, 2015, which claims priority to U.S. application No. 61/951,702, filed Mar. 12, 2014, the entire disclosures of each of which are hereby incorporated by reference.

FIELD OF THE INVENTION

The present invention relates to chemical synthesis, such as peptide synthesis, protein biosynthesis, or oligonucleotide synthesis. More specifically, the invention relates to an automatic gas valve container holder for solutions needed for such synthesis, and methods of synthesis using such an automatic gas valve container holder.

BACKGROUND OF THE INVENTION

There has been double digit growth for peptide therapeutics (Insulin excluded) during the last few years. The success of peptide pharmaceuticals kicked off once the issues with stability (shelf life) and fast degradation in the body were resolved. There are hundreds of trials on going in the advanced pre-clinical and clinical development phases. Almost 20 new APIs (Active Pharmaceutical Ingredient) entered clinical studies in 2010 compared to 5 new APIs/year in the 1980s. Synthetic peptides constitute the majority of both marketed peptides and peptides in the pipeline (about 70%). Peptide research and manufacturing are spread globally but the European and US markets that stand for the larger part of the totally estimated addressable market opportunity of $500 M/year for peptide API.

The benefits in using peptides as API in pharmaceuticals have been recognized for decades but have not been developed to its full capacity. Many functions have been identified but new therapeutic areas and indications are explored all the time. The advantages of peptides compared to the traditional small molecule are their high target specificity, higher potency and low toxicity. Any degradation products are amino acids which minimize any risks of systemic toxicity and their short $t_{1/2}$ (half-life) eliminates greater risks of being accumulated in tissues. The challenges of stability and short $t_{1/2}$ for peptides in the body have been met to a great extent.

Several synthesis technologies are available for polypeptide manufacturing. A simplified and brief summery is presented in Table 1. The quantities required, length of the peptide and its complexity influences the selection. A hybrid version may be developed to use the advantages of each individual technology. In the hybrid version, peptide fragments are synthesized using solid-phase technology and these are linked together to the correct full-length product using batch synthesis.

TABLE 1

| Peptide manufacturing technologies | | | |
|---|---|---|---|
| Technology | Sequence length | Scale | Comment |
| Solution-phase | ≤~15 AA | ≥100 kg | Might consume less solvent. In rare cases do not require chromatography purification. |
| Solid-phase | ≥~15 AA | ≤100 kg | Fastest and cheapest to process development. Can be used even for complex sequences. |
| Recombinant procedures | ≥~50 AA | ≤50-≥100 kg | Complex technology and expensive in time and resources required. Only applicable for natural peptide to date. |

Unlike the synthesis of oligonucleotides, a polypeptide synthesis system needs to be able to handle over 20 different amino acids, in addition to other chemical solutions. Furthermore, the amino acids in organic solvent need to be separated from air humidity as they are sensitive to water. There is thus a need for a compact container holder that provides these desired features.

BRIEF SUMMARY OF THE INVENTION

Disclosed herein includes a novel container holder which includes a gas valve that automatically opens when a container is connected to the container holder. When the container is disconnected, the gas control valve is closed automatically. Also disclosed are container holder panels that include at least two of the disclosed container holders, as well as methods of chemical synthesis which use such container holders and container holder panels to supply one or more amino acids.

Thus, a first aspect of the present invention is to provide a container holder, comprising a main body which in turn comprises
 (a) a gas inlet;
 (b) a solution outlet;
 (c) a gas control valve through which allows a gas to enter the container from the gas inlet; and
 (d) a sealing means for sealing the container in use, which sealing means includes a passageway for the input of the gas and for egress of a solution in the container;
wherein, when the container is sealingly connected to the container holder by the sealing means, the gas control valve opens automatically, and when the container is disconnected fluidically from the container holder the gas control valve is closed automatically.

A second aspect of the present invention is to provide a container holder panel, comprising two or more container holders according to the first aspect of the invention.

A third aspect of the present invention provides a method for chemical synthesizing, for example a polypeptide, comprising a cycling of synthesis steps:
(a) de-protection of alpha-amino protecting group on existing peptide;
(b) pre-activation of next amino acid in a mixer from a supply of amino acid; and
(c) coupling of activated amino acid to the existing peptide;

wherein at least one amino acid is supplied through a container connected to the container holder according to certain aspects of the invention.

Another aspect of the present invention provides a method for synthesizing a polypeptide, comprising a cycling of synthesis steps:
(a) de-protection of alpha-amino protecting group on existing peptide;
(b) pre-activation of next amino acid in a mixer from a supply of amino acid; and
(c) coupling of activated amino acid to the existing peptide;

wherein at least one amino acid is supplied through a container connected to the container holder panel according to certain aspects of the invention.

Further details and advantages of the present invention will appear from the description and claims below.

DETAILED DESCRIPTION OF THE INVENTION

One of the requirements for a polypeptide synthesis system relates to the need to be able to handle over 20 different amino acids, in addition to other chemical solutions. Furthermore, the amino acids in organic solvent need to be separated from air humidity as they are sensitive to moisture. A novel container holder is designed which includes a gas valve that automatically opens when a container is connected to the container holder. When the container is disconnected, the gas control valve is closed automatically. Such a container holder ensures that when a container including a composition that is sensitive to external environment is attached to the container holder, a small pressure is build t up in the container thus the composition is separated from the external environment. The invention further provides container holder panels that include at least two of the disclosed container holders, as well as methods of peptide synthesis which use such container holders or container holder panels to supply one or more amino acids.

Figure 1:
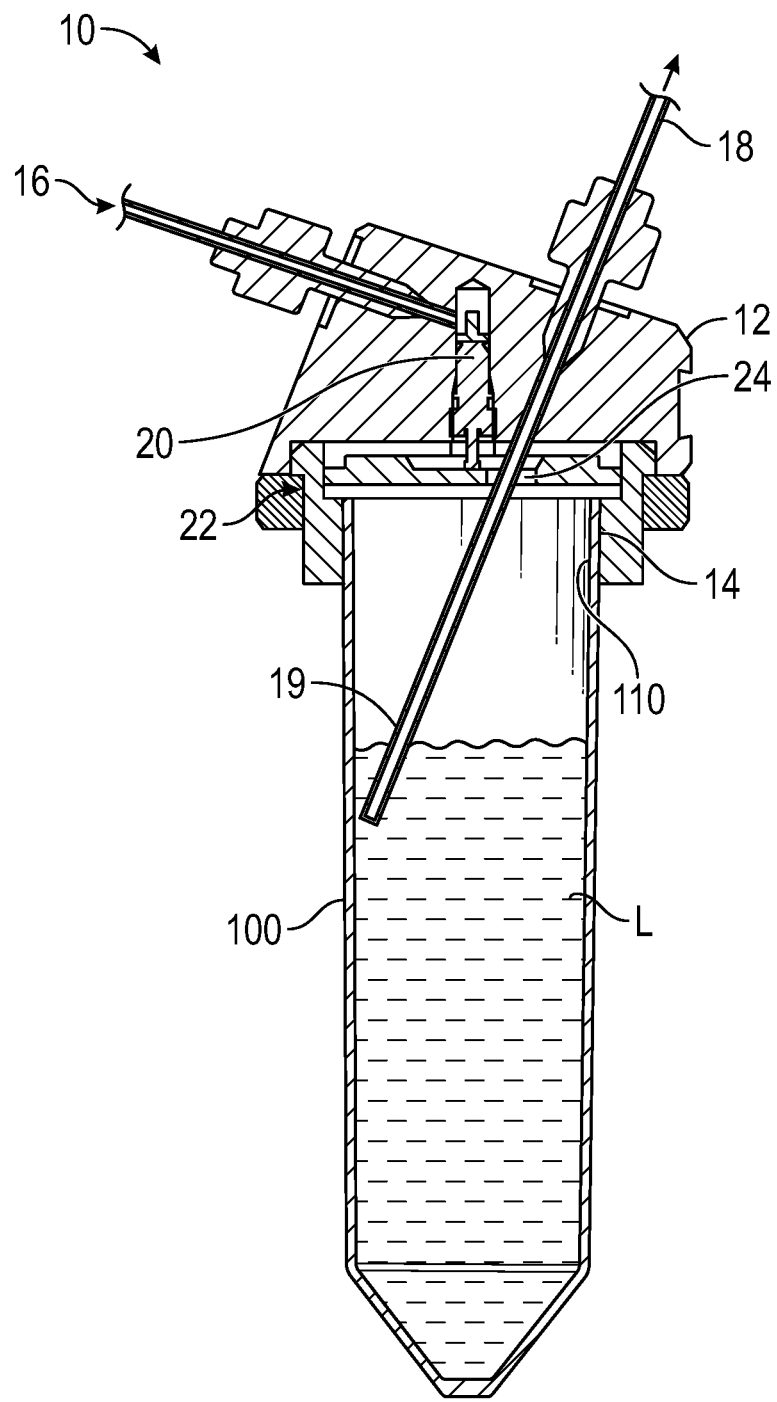
FIG. 1 shows a section view of container holder and a container in position. Gas is supplied through a capillary with the outer diameter 1/16" (1.6 mm) and similar capillary is used as an outlet for the amino acid.

In a first aspect, the present invention relates to a container holder 10 as exemplified in FIG. 1, for holding a container 100. The holder 10 comprises a main body 12 into which has an internally threaded aperture 14 facing downwardly for accepting the a complementarily threaded upper portion 110 of the container 100. The container holder main body 12 comprises also a gas inlet 16; a liquid solution outlet 18; a gas control valve 20 through which a gas enters the container 100 from the gas inlet 16; and a sealing means 22 for sealing the container when the container is screwed into the holder main body 10, which sealing means includes a passageway 24 for the input of gas and for an egress tube 19 which carries output liquid L solution from the container 100. The egress tube 19, which dips into a liquid L in the container, such that gas pressure from the gas inlet 16 will force the liquid L to travel up the egress tube 19 and exit the outlet 18. When a container is connected to the container holder, the gas control valve 20 opens automatically, and when the container is disconnected the gas control valve is closed automatically.

Figure 2:
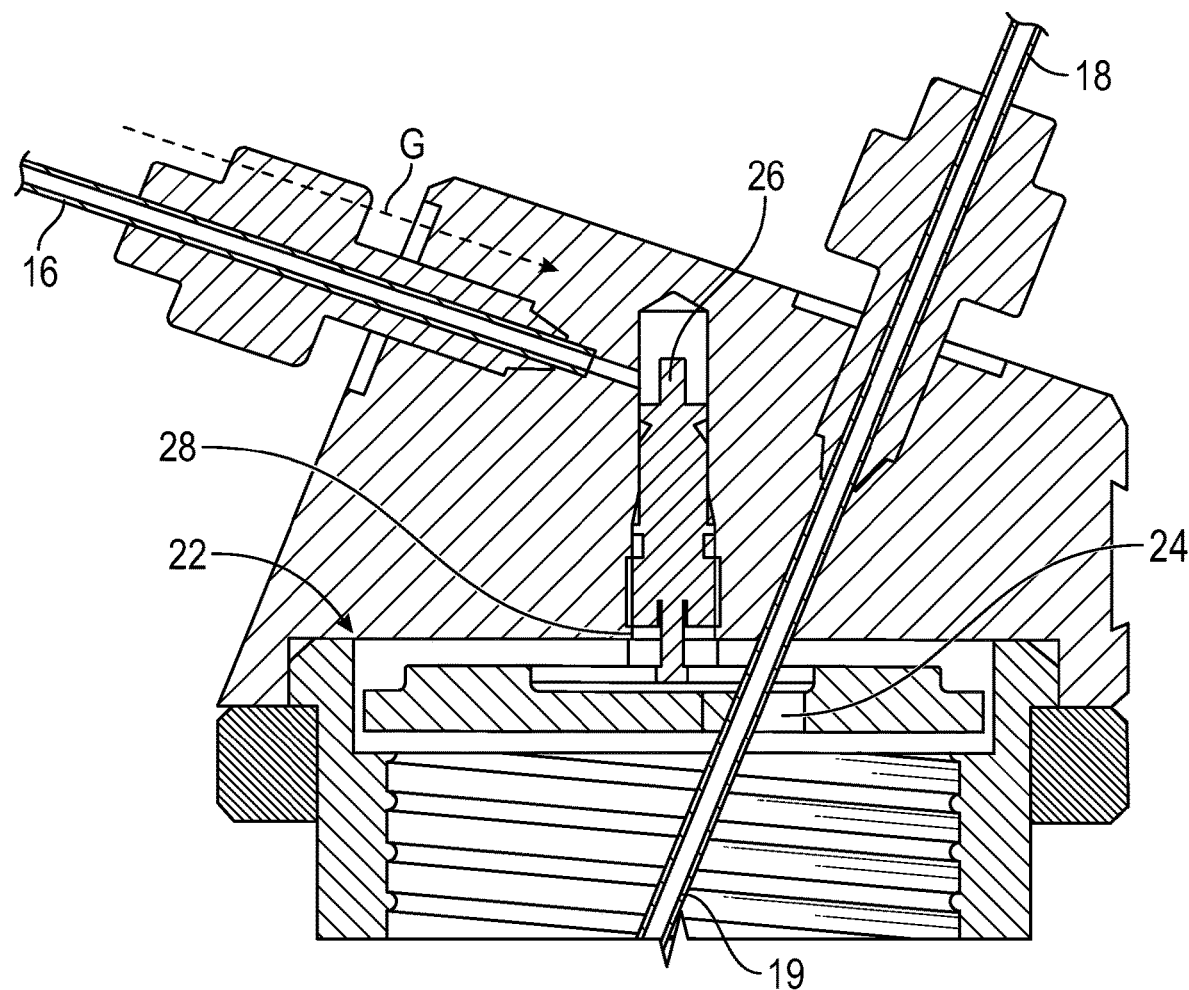
FIG. 2 shows a partial section side view of the container holder. The spring valve will be sealed by its internal O-ring.
Figure 3:
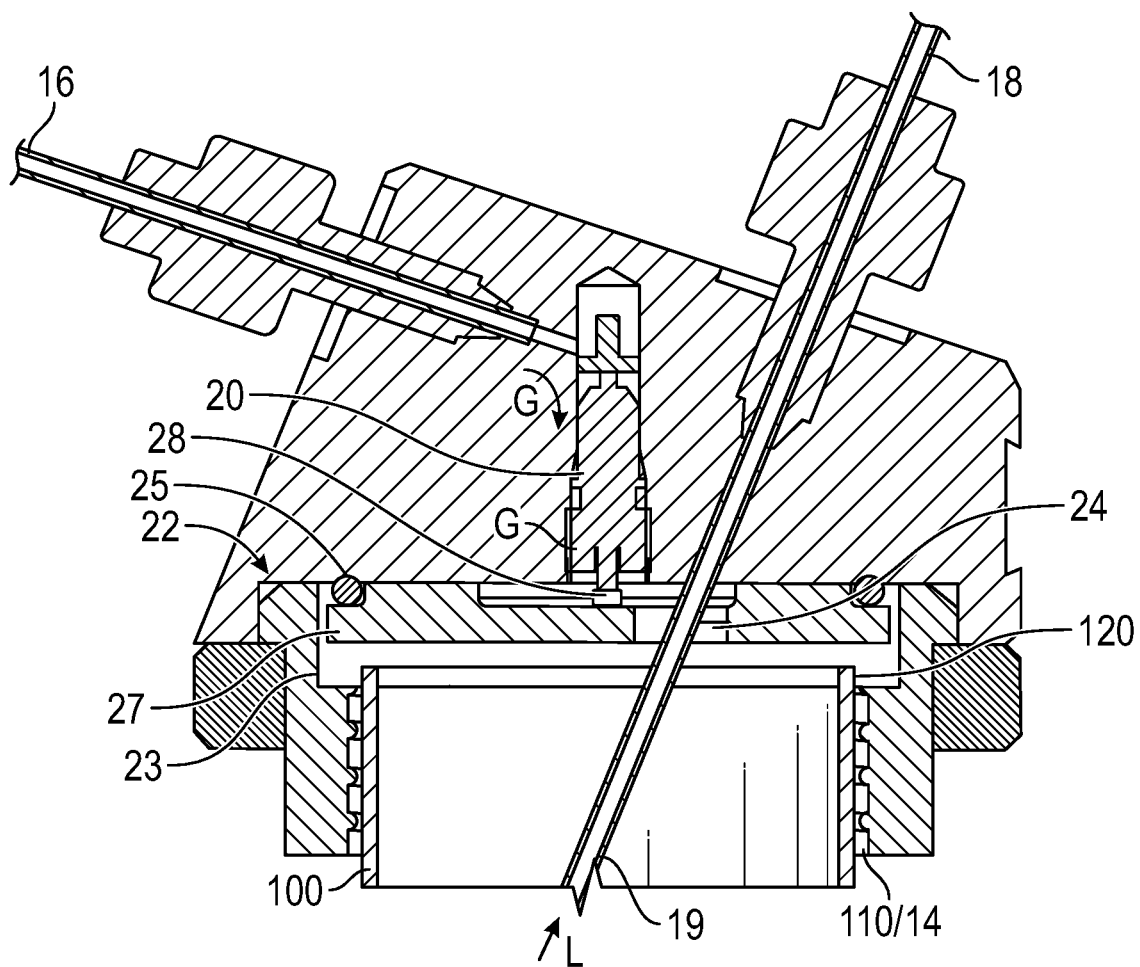
FIG. 3 shows a section side view. The spring valve is open and the gas will pressurize the container.

The operation of the gas valve is shown in more detail in FIGS. 2 and 3, where FIG. 2 shows the main body 12 of the holder, without a respective container attached thereto such that the gas valve 20 is closed, and FIG. 3 shows the main body with a container attached, such that the gas valve 20 is opened.

In more detail, when the container 100 is not threaded in position (FIG. 2), a spring-urged pin 28 of the valve 20 is forced downwardly so that gas G in the inlet 16 is blocked and cannot travel past an anti-chamber 26. When the container 100 is threaded into position an upper edge 120 of the container acts on an elastomeric flat seal member 23, which in turn forces a valve actuation plate 27 upwardly to act on the valve pin 29 and to force the pin upwardly against its spring urging. The valve 20 then opens and allows gas to pressurize the container 100. The back of the plate 27 is sealed against the main body 12 by an O ring seal 25.

It can be seen in FIG. 3 that the passageway 24 accommodates both the flow of pressurized gas G and the egress tube 19, providing a simple construction hat is easy to clean.

In one embodiment, the gas control valve 20 is a spring valve.

In one embodiment, the sealing means comprises a threaded part 14 and a plate 27 or disc, wherein when the container is connected with the threaded part through its threaded upper edge 120 or lid, the plate 27 or disc opens the gas control valve 20. The plate 27 or disc may be made of steel or plastic.

In certain embodiments, the container holder further comprises a flat seal 23 under the plate 27 or disc, and an O-ring 25 between the plate/disc and an inside surface or edge of the main body.

Figure 4:
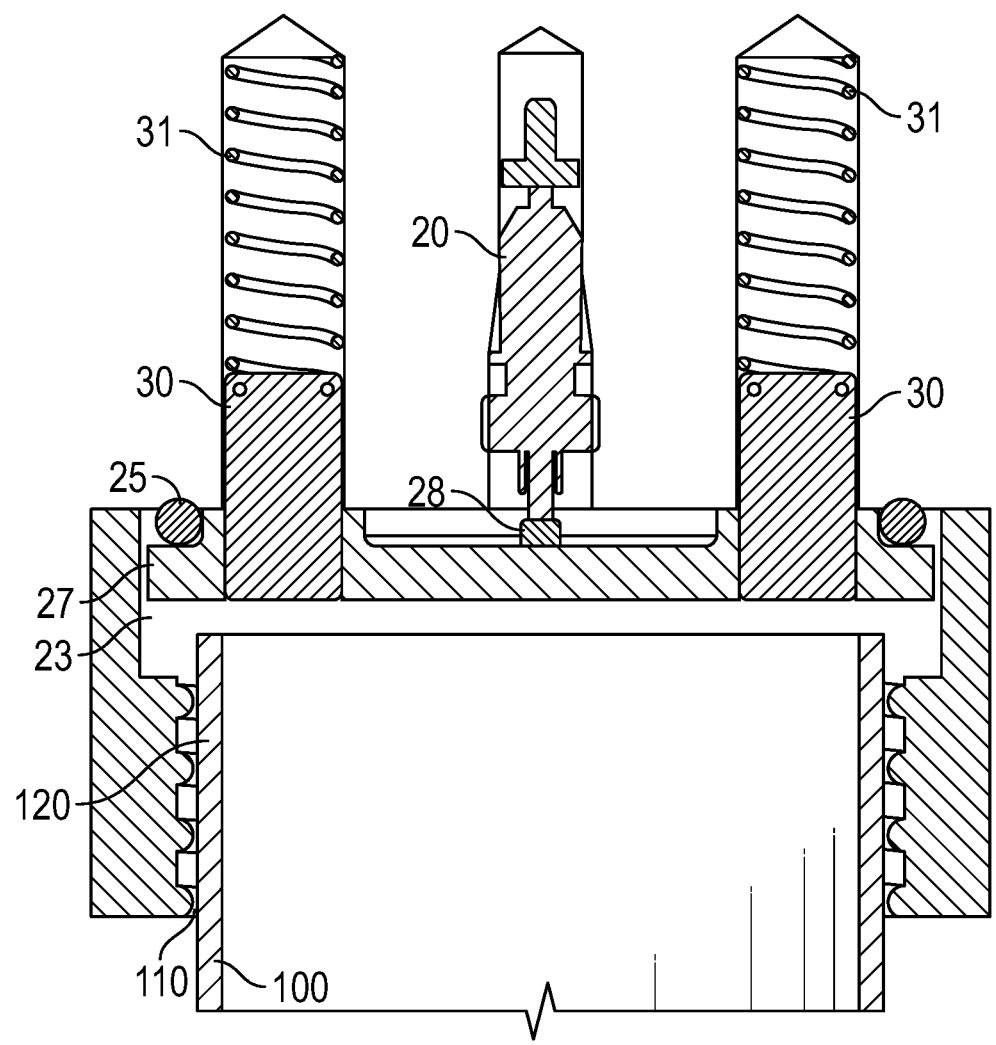
FIG. 4 shows a section front view. Guide pins prevent the steel disc to rotate when a tube is connected with its thread.

FIG. 4 shows a further sectional view of the main body 12, taken through a different sectional plane. In this view, guide pins 30 are shown urged into position by guide springs 31. The purpose of the guide pins 30 is to stop the plate 27 rotating when the container 100 is threaded into position into the main body 12.

In certain embodiments, a container used with the container holder may be of any shape or size, as long as the thread 110 matches that the thread 14 of the container holder. Alternatively, adaptor components with different threads for different containers may be used to connect different containers to different container holders. In a preferred embodiment, the containers are 50 ml tubes, such as Falcon tubes.

The container holder is designed such that when the gas control valve is in an open position, the container is pressurized with an inert gas and the solution in the container is insulated from external environment. In certain embodiments, the inert gas may be moisture-free. In certain other embodiments, the inert gas is nitrogen.

Figure 5:
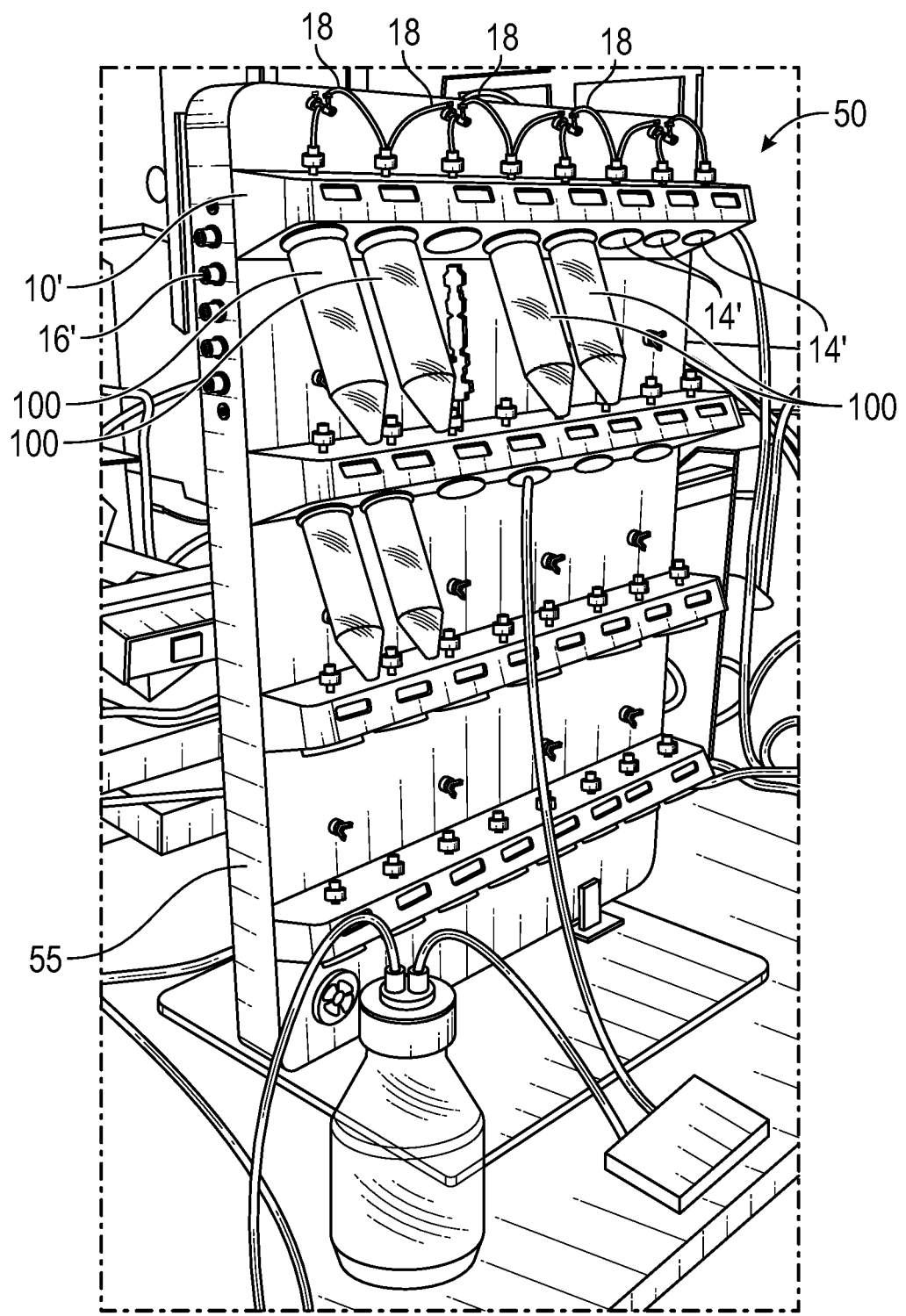
FIG. 5 shows an exemplary container holder with bench support.
Figure 6:
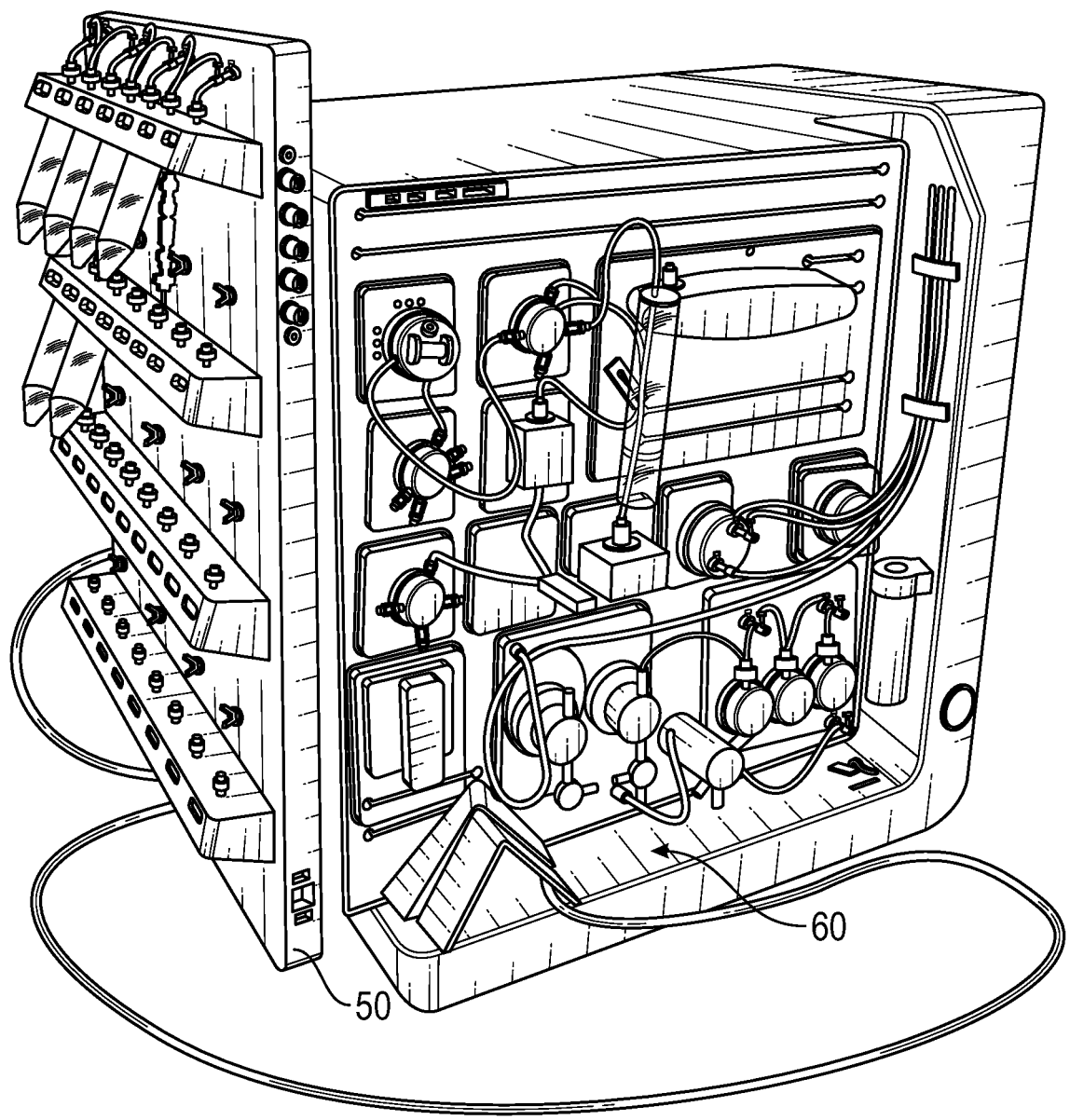
FIG. 6 shows an exemplary container holder attached to cabinet rail of a prototype polypeptide synthesizer.

A second aspect of the present invention is shown in FIGS. 5 and 6. A container holder panel 50 is shown, comprising a modified container holder which holds plural containers 100. The modified container holder 10' has multiple container accepting threaded apertures 14', a common gas inlet 16' and plural outlets 18. In FIG. 5 4 container holders 10' are shown, mounted one above another on a vertical support 55, to form a container holder panel 50.

In another exemplary embodiment, the present invention relates to a container holder panel 50 comprises at least two rows of container holders, each row with at least two container holders. In a preferred embodiment, the container holder panel comprises four rows of container holders, each row with 8 container holders.

In one embodiment, the gas inlets of each container holder are connected to a common gas source.

FIG. 6 shows the panel 50 in use with apparatus of chemical synthesis, such as polypeptide synthesis.

In certain embodiments, the container holder panel is used for supplying an amino acid solution to a peptide synthesizer 60. In certain preferred embodiments, the container holder panel 50 is used to supply all amino acid solutions needed for a polypeptide synthesis run to a peptide synthesizer 60.

In another aspect of the present invention, it is provided a method for synthesizing a polypeptide, comprising a cycling of synthesis steps:
(a) de-protection of alpha-amino protecting group on existing peptide;
(b) pre-activation of next amino acid in a mixer from a supply of amino acid; and
(c) coupling of activated amino acid to the existing peptide;
wherein at least one amino acid is supplied through a container connected to the container holder according to an aspects of the invention. In one exemplary embodiment, each amino acid is supplied through an individual container connected to a container holder.

In a third aspect of the present invention, it is provided a method for synthesizing a polypeptide, comprising a cycling of synthesis steps:
(a) de-protection of alpha-amino protecting group on existing peptide;
(b) pre-activation of next amino acid in a mixer from a supply of amino acid; and
(c) coupling of activated amino acid to the existing peptide;
wherein at least one amino acid is supplied through a container connected to a container holder of the container holder panel according to an aspects of the invention. In one exemplary embodiment, each amino acid is supplied through a container connected to a container holder of the container holder panel.

The cycling process for polypeptide synthesis is described below briefly.

An Exemplary Polypeptide Synthesis Process

A polypeptide may be synthesized on solid support packed in a column. The column volume, CV, required is related to the support's swelling properties and also the amount/length of the peptide to be produced. The support can either be added to the column in dry form or as slurry prior to setting up with the system. The synthesis process is a cyclic procedure where each cycle adds one amino acid to the growing peptide chain. The first amino acid (AA) might already be attached to the a-amine reaction sites on the support ready for the $2^{nd}$ AA to be coupled. For each cycle, different chemicals/reagents are pumped through the packed column in a stepwise manner.

Synthesis Steps

Each cycle comprises of:
De protection of a-amino protecting group on existing peptide in the column
Pre-activation of the next amino acid in the mixer
Coupling of the pre-activated amino acid with recirculation through the column
Optional capping step to block unbound amino acids in the end of the amino acid chain from binding to any amino acid throughout the subsequent synthesis steps.

The individual steps in each cycle are followed by a wash of the pathways and the column to eliminate any cross contamination and unwanted reactions. The cycles are repeated until the desired polypeptide product (amino acid chain) has been produced.

At start the intended sequence of AA is entered into the software together with information such as solid support to be used, the activation and coupling mixture intended for each AA coupling and also time for activation and coupling required respectively.

1. De protection of the last AA of the existing peptide will remove the Fmoc protection group. This is done by adding de-protective agent (piperidine for example) mixed with solvent (NMP or DMF usually). The column is flushed and the mixture is removed through the waste. The N-terminal is now free to react with the next AA which needs to be activated.

The pathways, column and mixer are washed with solvent (NMP or DMF usually).

2. Pre-activation of next AA to be coupled to the growing peptide is performed in a mixer. An additive and a base, if required for the AA to be activated, are added to the mixture together with the intended AA and a coupling reagent, CR. There are alternatives of additive, base and CR reagents and the choice depends on the specific AA and coupling to be made.

3. Coupling of the pre-activated amino acid is performed by pumping the coupling mixture through the column. This reaction is slow and recirculation is required for a high coupling degree.

This step is followed by a wash of the pathways, column and cleaning of the mixer to a detection level ≤0.01% of the AA being pre-activated.

Any non-reacted a-amines sites are sometimes required to be eliminated prior to addition of the next AA depending on the coupling to be performed. A capping agent is therefore optionally flushed through the column for this purpose.

The synthesis cycle continues for the next AA coupling.

Post-Synthesis

When synthesis is completed the column is dismantled from the system. The material is dried and the peptide is thereafter cleaved from the support prior to filtration/purification. The support remaining after the crude peptide has been cleaved off is discarded since it is a one-time use material.

A Container Holder

Each of the amino acids is dissolved in an organic solvent and needs to be protected from air humidity. This is achieved by pressurization of the container holding the AA solution with a small over pressure to ensure no air leakage into the container as it is being emptied during the peptide synthesis process. Pressurization of the container is achieved by connecting the container with a gas inlet on the bottle holder and then distributing an inert gas to the container. The gas flow is restricted through a spring valve to ensure no gas leakage when bottle is removed. When bottle is fully attached the spring valves' opening matches the gas inlet and gas is free to flow into the bottle. FIG. 1.

The container holders for the AA are important to have good usability and to assure the right functionality. Usability questions are connected to attaching and removing the containers from the flow path in an effective and robust way. Functionality regards mostly the need to keep the AA's free from moisture, but it might also be good to have some over pressure in the inlet tube to prevent cavitation due to the high viscosity in the AA solution.

The main body of the container holder are equipped with a gas control valve that opens when a container is fully connected (FIG. 2) and closes when a container is disconnected (FIG. 3).

When a container is connected with the container holder, the steel disc engages the spring valve to open the gas inlet and gas enters into the container through the oversized hole in the steel disc for the solution outlet. The gas flow into the tube is illustrated by green dashed arrows in FIG. 2. An O-ring and a flat rubber seal may be used to prevent gas leakage, see red and blue dashed circles in FIG. 2. The Fingertight 1/16" connectors (GE Healthcare) may be used for the gas inlet and amino acid outlet to prevent gas leakage.

When the container is not tightly connected with the container holder, the steel disc will fall down by gravity and the internal spring force inside the spring valve. The spring valve will be sealed by its internal O-ring, FIG. 3. The spring valve illustrated in FIGS. 1-4 is an exemplary Schrader valve, commonly used in automobile tires.

Optionally, two cylindrical guide pins are attached on the steel disc that prevents it from rotating which would otherwise cause the oversized hole for the amino acid outlet capillary to be out of position (FIG. 4). The guide pins may be provided with its own coil springs to thus support the internal spring of the spring valve (i.e., to assure proper return of the valve disc).

The automatic gas control system illustrated in FIGS. 1-4 provides added value by reduction of gas consumption as well as assuring gas flow when a container is in position. With the right sized connection, any container may be used with the container holder. A preferred container is the Falcon 50 ml tubes.

A Container Holder Panel for Use with a Polypeptide Synthesizer

Most polypeptides are composed of many different amino acids. Thus, a peptide synthesizer may need to be able to take in 20 or more different amino acids for a single polypeptide synthesizing run. Thus, 20 or more container holders may be needed for each synthesizing run. Instead of single container holders, it is therefore desirable to use a container holder panel, to better organize the amino acid and other solutions, and to minimize human intervention of the synthesis process.

Thus, a container holder panel may include two or more container holders. In one example, the container holder consists of 32 positions for standard 50 ml Falcon tubes and 10 Fingertight 1/16" connections (5 on either side of the panel) for supplying of an inert gas (e.g., $N_2$) to external, larger containers. The 32 positions for Falcon tubes are individually equipped with a gas control valve that opens when a tube is connected and closes when the tube is disconnected. The gas tubing may be integrated in the container panel wall, as part of the wall, or on the opposite side of the containers panel. The gas tubing may be anywhere as long as it does not interfere with the containers.

Connecting of a container with the corresponding container holder may be realized through screwing the thread on the container's lid with corresponding threaded part of the container holder. Thus, in one embodiment, some container holders of a container holder panel may have different types of threads for receiving different containers. In another embodiment, the container holders in a container holder panel have the same type of threads, and adaptor components with different threads for different containers may be used to connect different containers to the holders in a container holder panel.

A container holder panel may be a free standing unit with a support member (FIG. 5) or be placed on the cabinet rails (FIG. 6).

The containers connected to the gas inlets of either an individual container holder or a container holder panel may be pressurized with about 0.1 to about 0.5 bar using an inert gas, such as $N_2$. Although 50 ml Falcon tubes are preferred for the container holder panel, a container up to 200 ml may be used for a laboratory scale polypeptide synthesizer. To minimize weight and risk of cross contamination single use tubes of high chemical resistance plastic may be preferred.

While the particular embodiment of the present invention has been shown and described, it will be obvious to those skilled in the art that changes and modifications may be made without departing from the teachings of the invention. For example, peptide synthesis has been exemplified herein, although it will be apparent to the skilled addressee that the container holder described and illustrated will have broad applicability of use in other synthesis techniques such as synthesis of proteins or oligonucleotides. The matter set forth in the foregoing description and accompanying drawings is offered by way of illustration only and not as a limitation. The actual scope of the invention is intended to be defined in the following claims when viewed in their proper perspective based on the prior art.

We claim:

1. A container holder for holding a container, the container holder comprising a main body which in turn comprises:
   a gas inlet;
   a solution outlet comprising a solution egress tube;
   a gas control valve spaced from an entirety of the solution egress tube, and which allows a gas to enter the container from the gas inlet;
   a seal for sealing the container in use, having a passageway for the input of the gas and for the egress of a liquid in the container, a threaded part forming an internally threaded aperture of the main body complementary to a threaded part of the container and a valve actuation plate situated inside the threaded aperture of the main body;
   wherein, when the container is sealingly connected to the container holder by engaging the internal thread of the seal and the threaded part of the container and the container presses against the plate to force the plate, upwardly relative to the solution outlet to open the gas control valve automatically, and when the container is disconnected from the container holder, the plate returns back to its original position and the gas control valve is closed automatically.

2. The container holder of claim 1, wherein the gas control valve is a spring valve operable by means of the plate, in turn displaced by the act of sealingly connecting the container to the container holder.

3. The container holder of claim 1, wherein the plate includes a passage for fluidically interconnecting the container and the gas inlet, said passage accommodating said solution egress tube.

4. The container holder of claim 1, further comprising an elastomeric flat seal situated inside the aperture and under the plate, and an O-ring between the plate and an inside surface of the aperture.

5. The container holder of claim 1, further comprising one or more guide pins operable with the plate to prevent the plate from rotating when the container is sealingly connected to the container holder.

6. The container holder of claim 5, further comprising a coil spring for urging the guide pin into an operable position.

7. The container holder of claim 1, wherein at least some of the containers are 50 ml tubes.

8. The container holder of claim 1, wherein when the gas control valve is in an open position, the container is pressurizable with an inert gas and the solution in the container is insulated from its external environment.

9. The container holder of claim 8, wherein the inert gas is moisture-free.

10. The container holder of claim 8, wherein the inert gas is nitrogen.

11. A method of operating a synthesizer, the method comprising, using the container holder of claim 1 to supply an amino acid solution to the synthesizer.

12. A container holder panel, comprising two or more container holders of claim 1.

13. The container holder panel of claim 12, comprising at least two rows of container holders, each row comprising at least two container holders.

14. The container holder panel of claim 12, comprising four rows of container holders, each row including 8 container holders.

15. The container holder panel of claim 12, wherein the gas inlets of each container holder are connected to a common gas source.

16. A method of operating a synthesizer, the method comprising, using the container holder panel of claim 12 to supply at least one amino acid solution to a peptide synthesizer.

17. A method for synthesizing a polypeptide using the container holder of claim 1, the method comprising a cycling of synthesis steps:
(a) de-protection of an alpha-amino protecting group on an existing peptide;
(b) pre-activation of an amino acid in a mixer to form a pre-activated amino acid; and
(c) coupling of the pre-activated amino acid to the existing peptide;
wherein the amino acid is supplied through a container connected to the container holder of claim 1.

18. A method for synthesizing a polypeptide using the container holder panel of claim 12, the method comprising a cycling of synthesis steps:
(a) de-protection of an alpha-amino protecting group on an existing peptide;
(b) pre-activation of an amino acid in a mixer to form a pre-activated amino acid; and
(c) coupling of the pre-activated amino acid to the existing peptide;
wherein the amino acid is supplied through a container connected to a container holder of the two or more container holders of the container holder panel of claim 12.

19. The method of claim 16, wherein each amino acid solution of the at least one amino acid solution is supplied through a respective container connected to a respective container holder of the container holder panel of claim 12.

20. A container holder for holding a container, the container holder comprising a main body which in turn comprises:
a gas inlet;
a solution egress tube;
a solution outlet fluidically coupled to the solution egress tube;
a gas control valve spaced from an entirety of the solution egress tube and the solution outlet, and which allows a gas to enter the container from the gas inlet;
a seal for sealing the container in use, having a passageway for the input of the gas and for the egress of a liquid in the container, a threaded part forming an internally threaded aperture of the main body complementary to a threaded part of the container and a valve actuation plate situated inside the threaded aperture of the main body; and
an elastomeric flat seal situated under the plate inside the aperture,
wherein, when the container is sealingly connected to the container holder by engaging the internal thread of the seal and the threaded part of the container, the container presses against the elastomeric flat seal which in turn presses against the plate to form the plate, upwardly relative to the solution outlet to open the gas control valve automatically, and when the container is disconnected from the container holder, the plate returns back to its original position and the gas control valve is closed automatically.

* * * * *